US00PP20411P2

(12) United States Plant Patent
Laviana

(10) Patent No.: US PP20,411 P2
(45) Date of Patent: Oct. 13, 2009

(54) *ECHINACEA* PLANT NAMED 'RED KNEE HIGH'

(50) Latin Name: *Echinacea purpurea*
Varietal Denomination: Red Knee High

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 0 days.

(21) Appl. No.: 12/286,720

(22) Filed: Oct. 1, 2008

(51) Int. Cl.
*A01H 5/00* (2006.01)

(52) U.S. Cl. ..... Plt./428

(58) Field of Classification Search ..... Plt./263, Plt./428
See application file for complete search history.

*Primary Examiner*—Susan B McCormick Ewoldt
(74) *Attorney, Agent, or Firm*—Penny J. Aguirre

(57) ABSTRACT

A new cultivar of hybrid *Echinacea*, 'Red Knee High', characterized by its compact and dwarf growth habit, its sturdy stems, its inflorescences with ray florets that emerge bright red-purple surrounding golden yellow cones and fade to pink as they mature, its continuous bloom from mid summer through fall, its ease of propagation, its vigorous growth habit, and its hardiness in U.S.D.A. Zones 3 to 8.

2 Drawing Sheets

Botanical classification: *Echinacea purpurea.*
Variety denomination: 'Red Knee High'.

BACKGROUND OF THE INVENTION

The present invention relates to a new and distinct cultivar of *Echinacea purpurea* and will be referred to hereafter by its cultivar name, 'Red Knee High'. 'Red Knee High' represents a new purple coneflower, an herbaceous perennial grown for landscape use.

The new Invention arose as a naturally occurring branch mutation of *Echinacea purpurea* 'Kim's Knee High' (U.S. Plant Pat. No. 12,242) in a container growing outdoors in the Inventor's nursery in Kensington, Conn. in August of 2005.

Asexual reproduction of the new cultivar was first accomplished by in vitro propagation in Rijswijk, The Netherlands in 2007 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Red Knee High' from other cultivars of *Echinacea* known to the inventor.

1. 'Red Knee High' exhibits a dwarf plant habit, reaching a height of 45 to 60 cm (18 to 24 inches).
2. 'Red Knee High' composite flowers with ray florets that open bright red-purple in color surrounding golden colored cones with the ray florets fading to pink as they mature.
3. 'Red Knee High' is readily propagated by tissue culture and has a vigorous growth habit.
4. 'Red Knee High' blooms continuously from mid summer through fall.
5. 'Red Knee High' is reliably hardy in U.S.D.A. Zones 3 to 8.

The new cultivar is similar to its parent plant, 'Kim's Knee High' in having a dwarf plant habit, however 'Kim's Knee High' differs in having inflorescences with ray florets that are lighter and less red in color and cones that are more reddish brown in color. 'Red Knee High' can also be compared to *Echinacea* 'CBG Cone 2' (U.S. Plant Pat. No. 18,546), which is also similar to 'Red Knee High' in having a dwarf plant habit, however 'GBC Cone 2' differs from 'Red Knee High' in having ray floret that are held more horizontally and are lighter and medium pink in color.

BRIEF DESCRIPTION OF THE DRAWING

The plants and plant parts in the accompanying photographs depict a two year-old plant of 'Red Knee High' as grown in a garden in Kensington, Conn.

The photograph in FIG. 1 depicts a plant of 'Red Knee High' in peak bloom.

Figure 1:
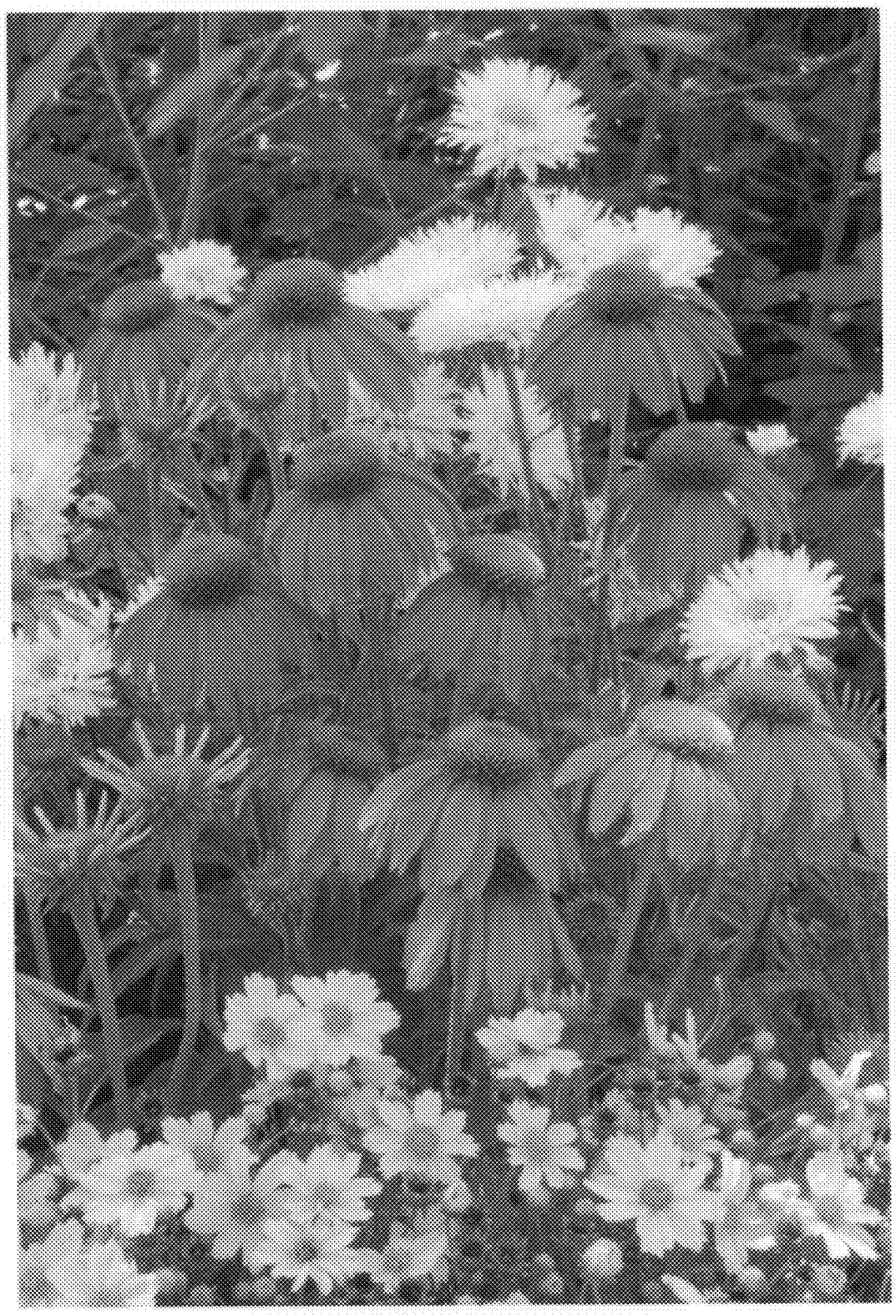
Figure 2:
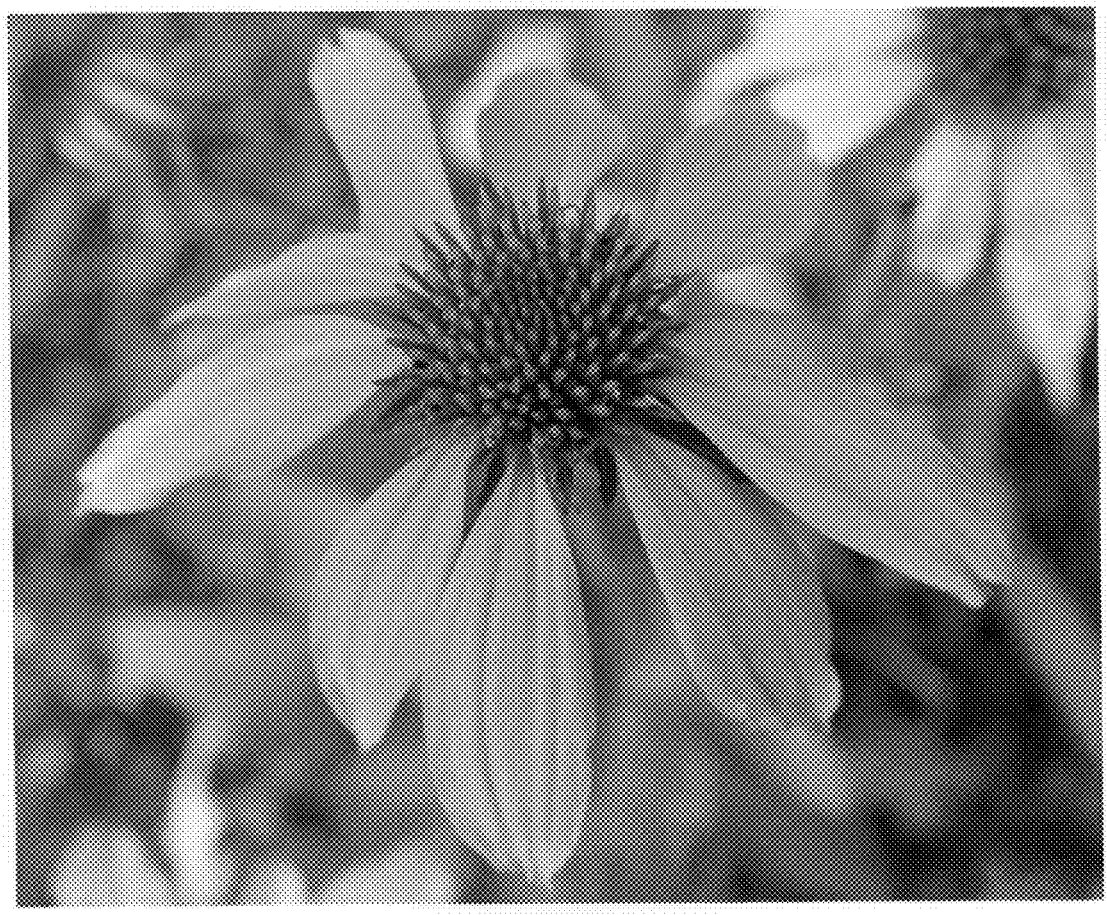

The photograph in FIG. 2 shows a close-up of an inflorescence as it matures.

The Colors in the photograph may differ slightly from the color values cited in the detailed botanical description, which accurately describe the colors of the new *Echinacea.*

BOTANICAL DESCRIPTION OF THE PLANT

The following is a detailed description of a one-year-old plant of the new cultivar as grown in a garden in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from mid-summer to fall.

*Plant habit.*—Herbaceous perennial, clump-forming, upright, loosely but freely branched.

*Height and spread.*—Reaches 45 to 60 cm in height and 30 to 45 cm in spread.

*Hardiness.*—U.S.D.A. Zones 3 to 8.

*Culture.*—Tolerant to a wide range of growing conditions, growing well in full sun to light shade, in dry to moist soils.

*Diseases and pests.*—No susceptibility or resistance to diseases or pests has been observed.

*Root description.*—Fibrous.

Growth and propagation:

*Propagation.*—Division, vegetative stem cuttings, and tissue culture.

*Growth rate.*—Vigorous.

Stem description:

*Shape.*—Slightly oval, solid.

*Stem color.*—144A.

*Stem size.*—Average of 3.5 mm in diameter and an average of 29 cm in height including peduncle.

*Stem surface.*—Moderately covered with short stiff white hairs about 1.5 mm in length.

*Stem number.*—About 4 as grown in a two-quart container.

*Internode length.*—Typically 1.5 to 3 cm in length.

*Branching.*—Un-branched.

Foliage description:

*Leaf shape.*—Lanceolate.

*Leaf division.*—Simple.

*Leaf base.*—Cuneate to long leaf-like petiole.

*Leaf apex.*—Acuminate.

*Leaf venation.*—Tri-nerved, upper surface 145B to 145C in color, lower surface mid rib is prominent and 145C in color.

*Leaf margins.*—Entire and ciliate.

*Leaf attachment.*—Petiolate.

*Leaf arrangement.*—Alternate.

*Leaf size.*—Matures to an average of 9 cm in length and 2.8 cm in width.

*Leaf color.*—Newly formed and mature, upper surface; 137B, newly formed and mature lower surface; a color between 138B and 138C.

*Leaf surface.*—Upper surface dull and finely puberulent and rough to touch, lower surface is finely puperulent but glaucous in appearance.

*Petioles.*—Leafy and extended from leaf blade, range from 1.5 cm to 4 cm in length, typically about 5 mm in width at leaf blade and about 3.5 mm in width at stem, recurved inward on upper surface, 137B in color on leafy edges and center portion is 145C on both surfaces.

Flower description:

*Type.*—Capitulum, heterogamous with ray florets around the head margin and disk florets in the center, forming a radiant head.

*Capitulum number.*—One terminal capitulum per stem.

*Lastingness of inflorescence.*—About 10 days until senescence of ray flowers, disk flowers are persistent.

*Capitulum size.*—Matures to about 1.5 cm in depth and 7 cm in diameter, disk size is about 8 mm in depth and 1.8 cm in diameter.

*Fragrance.*—None.

*Involucral bracts or phyllary.*—About 40 arranged in 3 overlapping rows, up to 8 mm in length and 2 mm in width, fused at base, acute apex, lanceolate in shape, 137A to 137B in color, entire ciliate margin and glabrous on both surfaces.

*Buds.*—Cup-shaped, up to 2.3 cm in diameter and 1.5 cm in height, phyllary is 137A to 137B in color, ray florets are 145A slightly flushed with 62B and disk flowers appear 137B in color when viewed in mass just prior to opening.

*Peduncle.*—Strong, sometimes curved, continuous with stem, typically 8 to 10 cm in length and an average of 2.5 mm in diameter widening to about 4.5 mm at base of capitulum, 144A in color, texture is rough with short stiff white hairs.

*Ray florets* (*sterile*).—About 20, oblong in shape, vertical ridges on both surfaces, about 2.8 cm in length and 7 mm in width, emarginated apex, truncate base, entire margin except apex, glabrous in texture, initially held upright about 70° from horizontal and become horizontal, then slightly reflexed as they mature, color of upper and lower surface when just opening; 155A with an overlay of 62B with very end of tips N77A, color of upper surface when fully open; blend of 64A and 64B, color of lower surface when mature; blend of 73B and 73C with center a blend of 138B and 73D and thin margins of 64B, upper surface fades to 70B and then to a blend of N78C and 78D, lower surface fades to blend of N78D, 159D and 138B.

*Disk flowers* (*bisexual*).—Numerous, about 150, tubular in shape, arranged spirally on a conical receptacle, about 1 cm in length and 2 mm in width, surrounded by a pale; 8 mm in length and 1.5 mm in width, lanceolate in shape with an apex that terminates in a spine, color is 144B to 144C with an a spiny apex of 21B (yellow-orange), petals (5) are fused into tube about 6 mm in length and 1.7 mm in width and 145B in color.

Reproductive organs (present on disk florets only):

*Gynoecium.*—Pistil; 1, 8 mm in length and 1.5 mm in width, style; 0.3 mm in width and 4 mm in length, 1D in color, surrounded by stamens, stigma; bifid, each arm is reflexed, about 2.5 mm in length and 176A in color, ovary; inferior, single-celled, 0.4 mm in diameter, 144A in color.

*Androcoecium.*—Stamens; 5, fused, form a cylinder around style, 4 mm in length and 0.7 mm in width, dehisced longitudinally, 200A in color filaments; 1.5 mm in length, 0.5 m in width, 1D in color, pollen; moderate in quantity and 17B in color.

*Fruit.*—An achene, 5 mm in length and 0.8 mm in width, 200B in color.

It is claimed:

1. A new and distinct cultivar of *Echinacea* plant named 'Red Knee High' substantially as herein illustrated and described.

* * * * *